United States Patent [19]

Egalon et al.

[11] Patent Number: 5,262,638

[45] Date of Patent: Nov. 16, 1993

[54] OPTICAL FIBERS AND FLUOROSENSORS HAVING IMPROVED POWER EFFICIENCY AND METHODS OF PRODUCING SAME

[75] Inventors: Claudio O. Egalon; Robert S. Rogowski, both of Hampton, Va.

[73] Assignee: The United States of America as represented by the United States National Aeronautics and Space Administration, Washington, D.C.

[21] Appl. No.: 761,198

[22] Filed: Sep. 16, 1991

[51] Int. Cl.[5] ............................................. G01N 21/00
[52] U.S. Cl. ................................. 250/227.14; 385/12
[58] Field of Search ............. 250/227.14, 458.1, 459.1, 250/461.1, 461.2; 385/12, 123, 125, 144

[56] References Cited

U.S. PATENT DOCUMENTS

| | | | |
|---|---|---|---|
| 4,755,667 | 7/1988 | Marsoner et al. | 250/461.1 |
| 4,834,496 | 5/1989 | Blyler, Jr. et al. | 350/96.29 |
| 4,844,869 | 7/1989 | Glass | 250/227.25 |
| 4,846,548 | 7/1989 | Klainer | 350/96.29 |
| 4,852,967 | 8/1989 | Cook et al. | 385/123 |
| 4,867,559 | 9/1989 | Bach | 250/458.1 |
| 4,880,752 | 11/1989 | Keck et al. | 435/7 |
| 4,889,690 | 12/1989 | Opitz et al. | 385/12 |
| 4,945,245 | 7/1990 | Levin | 250/461.2 |
| 5,039,490 | 8/1991 | Marsoner et al. | 250/216 |
| 5,061,857 | 10/1991 | Thompson et al. | 250/458.1 |

OTHER PUBLICATIONS

Lieberman, et al., "A distributed fiber optic sensor based on cladding fluoresence", J. Lightwave Tech. vol. 8, No. 2, Feb. 1990, pp. 212–220.

Marcuse, D., "Launching light into fiber cores from sources located in the cladding", J. Lightwave Tech., vol. 6, No. 8, Aug. 1988, pp. 1273–1279.

Love, Walter F., et al., "Optical characteristics of fiber-optic evanescent wave sensors", Biosensors with Fiber-optics, Wise and Wingard eds. *The Humana Press, Inc.*, 1991, pp. 139–180.

*Primary Examiner*—David C. Nelms
*Assistant Examiner*—John R. Lee
*Attorney, Agent, or Firm*—Kevin B. Osborne

[57] ABSTRACT

An optical fiber fluorosensor is provided having a portion of a fiber core which is surrounded by an active cladding which is permeable by the analyte to be sensed and containing substances which emit light waves upon excitation. A remaining portion of the fiber core is surrounded by a guide cladding which guides these light waves to a sensor which detects the intensity of waves, which is a function of the analyte concentration. Contrary to conventional weakly guiding principles, the difference between the respective indices of refraction of the fiber core and the cladding is greater than approximately 0.01. In an alternative embodiment, the fiber core is surrounded by an active cladding which is thin enough such that its index of refraction is effectively that of the surrounding atmosphere, whereby the atmosphere guides the injected light throughout the fiber core.

18 Claims, 3 Drawing Sheets

OPTICAL FIBERS AND FLUOROSENSORS HAVING IMPROVED POWER EFFICIENCY AND METHODS OF PRODUCING SAME

ORIGIN OF THE INVENTION

The invention described herein was jointly made in the performance of work under a NASA contract and an employee of the United States Government. In accordance with 35 U.S.C. 202, the contractor elected not to retain title.

BACKGROUND OF THE INVENTION

1. Technical Field of the Invention

The present invention relates generally to an optical fiber fluorosensor and more particularly an improved fluorosensor capable of determining the concentration of any chemical species.

2. Discussion of the Related Art

Absorption and emission of evanescent waves are well-known phenomena that have been theoretically and experimentally investigated and widely used for sensing purposes. For example, absorption of evanescent waves is used to determine the concentration of methane-gas with a tapered optical fiber. In this approach, a He-Ne laser excites bound modes in the fiber. The chemical species surrounding the tapered region of the fiber absorbs the evanescent wave associated with these modes at a specific wavelength. This absorption can be detected at the end of the fiber as a decrease in the output signal level and the concentration of the species inferred.

Using evanescent wave coupling, an optical fiber sensor has been developed with a fluorescent cladding to detect molecular oxygen. Evanescent waves are a factor whenever radiation is totally internally reflected between two dielectric media having different indices of refraction. Although most of the incident power is reflected, part of the radiation, termed the evanescent component of the field, penetrates a very thin layer of the dielectric having the lower index of refraction. Specifically, an optical fiber is clad during manufacture with a polymer such as polydimethyl siloxane which has a fluorescent dye dissolved therein. The dye itself is sensitive to the presence of molecular oxygen. The fluorescent cladding was excited via evanescent waves upon side-illumination at a wavelength within the excitation range of the dye. As before, some light was trapped in the core by evanescent coupling. In a similar sensor, an oxygen sensitive fluorescent coating was applied to a fiber having a fluorescent core. The light emitted by the dye in the cladding excited the fluorescent sources in the core. The result was a 100-fold increase in the efficiency of the sensor when compared with the previous one. The fluorescence intensity is a measure of the partial pressure of molecular oxygen.

These conventional fluorosensors are characterized by the weakly guiding approximation, which is also used to model communications fibers. This approximation is based on the assumption that small differences of approximately 0.01 or less between the respective index of refraction for a fiber core and a cladding are desired. This small difference in effect confines the optical model to one index of refraction, whereas a true optical fiber has two indices of refraction.

In addition, geometric optics theory has been employed to determine chemical concentration. However, this method cannot be applied to fibers having a few modes. Also, this method concentrates solely on the corpuscular nature of light whereas the injection of light from cladding sources is properly characterized as a wave phenomenon.

OBJECTS OF THE INVENTION

It is accordingly an object of the present invention to improve an optical fiber for use in fluorosensing.

It is another object of the present invention to produce an optical fiber fluorosensor which accounts for different indices of refraction between a fiber core and cladding.

It is a further object of the present invention to allow optical fiber with large differences in refraction indices to be used in fluorosensing.

It is another object of the present invention to allow optical fibers with a few modes to be used in fluorosensing.

It is a further object of the present invention to account for the wave phenomena characterization of light injection from a cladding source.

Other objects and advantages of the present invention are apparent from the following discussion with reference to the drawings.

SUMMARY OF THE INVENTION

The foregoing and additional objects are obtained by an optical fiber, and specifically an optical fiber fluorosensor, according to the present invention. A portion of a fiber core is surrounded by an active cladding which is permeable by the analyte to be sensed and having substances which emit light waves upon excitation. A remaining portion of the fiber core is surrounded by a guide cladding which guides these light waves to a sensor which detects the intensity of waves, which is a function of the analyte concentration. Contrary to conventional weakly guiding principles, the difference between the respective indices of refraction of the fiber core and the cladding is greater than approximately 0.01.

In an alternative embodiment, the fiber core is surrounded by an active cladding which is thin enough such that its index of refraction is effectively that of the surrounding atmosphere, whereby the atmosphere serves as an effective cladding to guide the light into and throughout the core.

DETAILED DESCRIPTION

Figure 1:
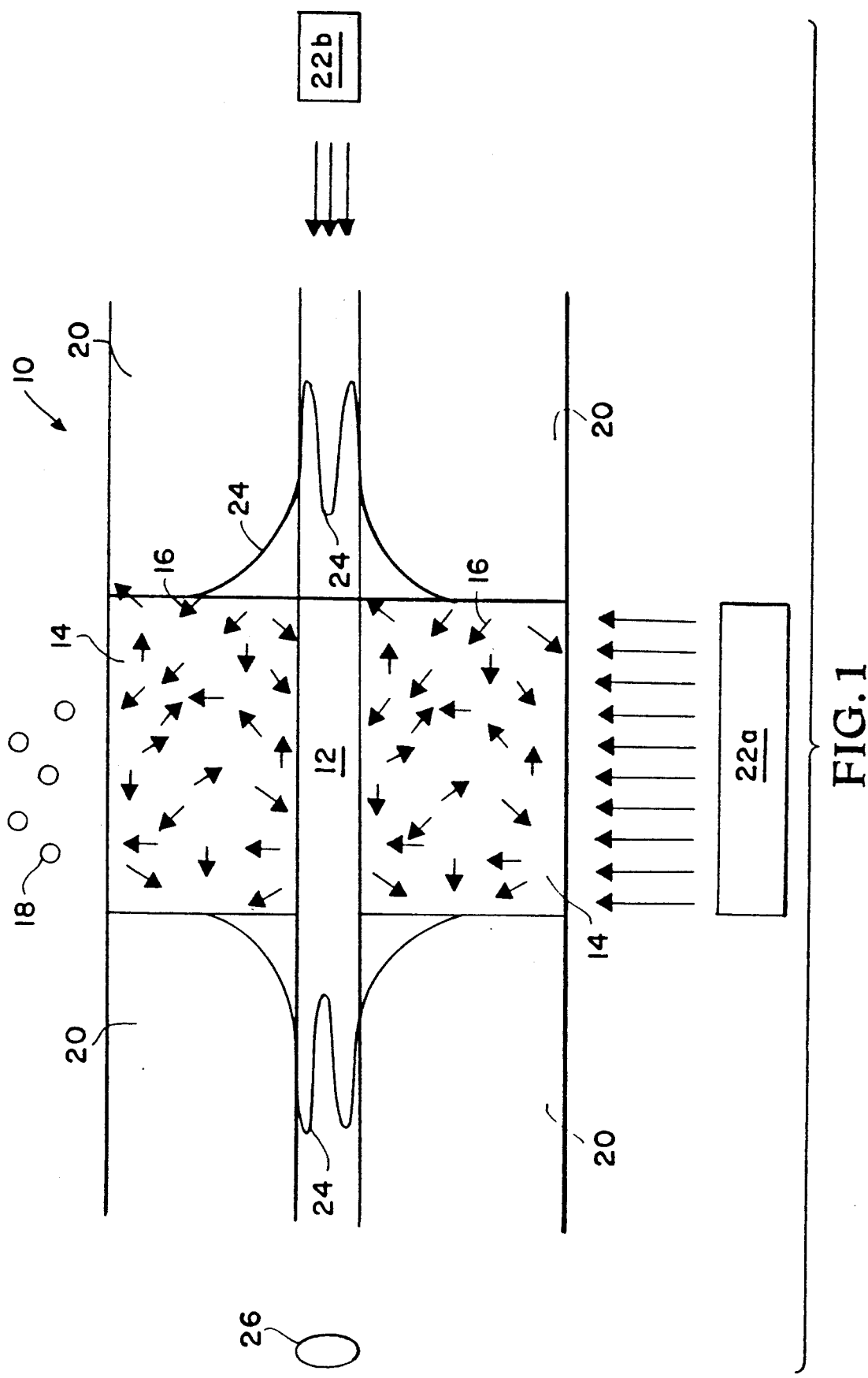
FIG. 1 is an exposed side view of an optical fiber fluorosensor according to the present invention.
Figure 2:
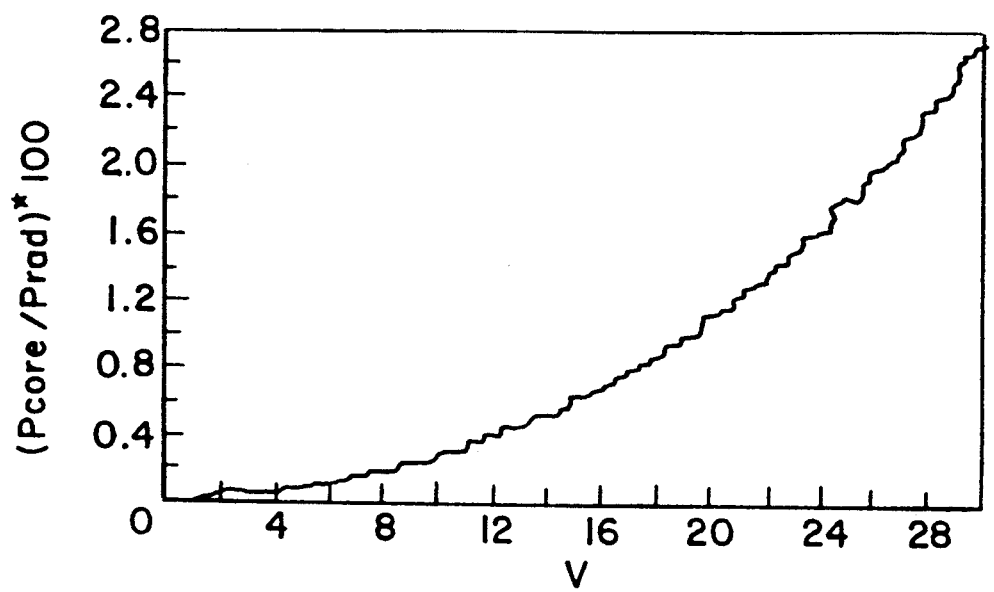
FIG. 2 is a graph of the power efficiency for an optical fluorosensor versus V-number.

An active cladding step index profile optical fiber, also known as a distributed sensor, is generally designated by reference numeral 10 in FIG. 1. Optical fiber 10 is used to provide information of a chemical species or analyte via evanescent wave interection. The optical fiber 10 comprises a core fiber 12, a portion of which is cladded or coated with a matrix 14, e.g., a polymer, which has fluorescent or chemiluminescent substances 16 dissolved therein. As discussed below, fluorescent or chemiluminescent substances 16 can be modeled as dipole sources that are uniformly distributed in the cladding matrix 14 and have random phase and orientation. The matrix 14 is permeable to the particular chemical species or analyte 18 being sensed and the fluorescent or chemiluminescent substances 16 interact selectively with chemical species or analyte 18.

If substance 16 is chemiluminescent, substance 16 is excited to emit light via a chemical reaction with the analyte 18. If substance 16 is fluorescent, excitation is accomplished via an outside light source 22a which illuminates the side of matrix 14 or by an outside light source 22b which injects light into one end of core 12 via evanescent wave absorption. Regardless of the excitation method, substance 16 produces light 24 which is injected into core 12 and guided throughout the core 12 via inactive guide cladding 20 to a light detector 26 for appropriate analysis. Guide cladding 20 and matrix 14 have equivalent outer radii. The intensity of the detected signal is a function of the concentration of the particular chemical species or analyte 18 which permeates matrix 14.

A cylindrical optical waveguide can support two kinds of modes: radiation and bound modes. The total electromagnetic fields of waveguide can be expressed as a sum of these two modes. In ray theory, light beams that have an incident angle smaller than the critical angle correspond to the radiation field. Those are the refracted rays. On the other hand, electromagnetic fields that propagate indefinitely inside the waveguide structure are expressed as bound modes. In general, most of the bound mode energy propagates inside the core of the fiber. The portion that penetrates into the guide cladding 20, i.e., the region having the lower index of refraction, is termed the evanescent field. There is no ray counterpart for the evanescent field. However, for those fields that are not evanescent their geometrical counterpart are represented by rays that are totally internally reflected, having an angle of incidence greater than the critical angle.

Bound and radiation modes are excited by injecting electromagnetic energy from sources into the fiber. Lasers, diodes and fluorescent molecules can be used for this purpose. Only the excitation of an optical fiber due to sources distributed in the cladding is of importance.

Excited sources distributed in the cladding of an optical fiber generate radiation fields and can inject bound modes. For sensing purposes, bound modes are more important. They propagate indefinitely in the core of the fiber and can be easily collected for analysis. In addition to that, any pertubation to the trapped field produces information regarding the surroundings of the fiber. The bound modes excited by the sources in the fiber cladding are closely related to the evanescent field. Without evanescent fields, bound modes cannot be excited from sources in the cladding.

As noted in the Background section, conventional optical fibers are modeled using a week guidance condition wherein a small difference exists between the index of refraction of the fiber core, $n_{core}$, and the index of refraction of the cladding matrix, $n_{clad}$, i.e., $n_{core} \approx n_{clad}$. This difference is conventionally less than 0.01. Using this relationship, the graph in FIG. was generated, wherein the following variables are employed:

$P_{core}$—total power in core fiber 12
$P_{rad}$—total power radiated by the substances 16 in cladding matrix 14

The following quantities were held constant:
λ of light wave = 1. μm
$n_{core}$ = 1.46
a, radius of core 12 = 10.0 μm
radius of guide cladding 20 = 50.0 μm Rather than calculating the P values by varying the V-number in the conventional manner independently of $n_{core}$ and $n_{clad}$, $n_{clad}$ was varied from 1.4599 at V=0.05 to 1.322 at V=29.95. This variance resulted in an increasing difference ep between $n_{core}$ and $n_{clad}$ in contrast to the no difference, or very small difference, assumption of conventional weakly guiding approximation. The model for this fiber is accordingly a positively guiding fiber, $n_{core} > n_{clad}$.

The power efficiency for a fiber coated with fluorescent or chemiluminescent sources in the core/cladding interface is given by $$\frac{P_{core}}{P_{rad}} = \frac{\sqrt{\epsilon_0 \mu_0}}{8 a \delta L n_{clad} k^2} \sum_{\nu,\mu} \frac{1}{P_{\nu,\mu}} \int_{v_{source}} |e_{\nu,\mu}|^2 dV \quad (1)$$

where L is the length of the fiber which is coated with sources, k is the circular wave number of the emitted light and δ is the thickness of the fluorescent of chemiluminescent film which is very small, e.g., $\delta << a/W_{\nu,\mu}$.

Figure 3:
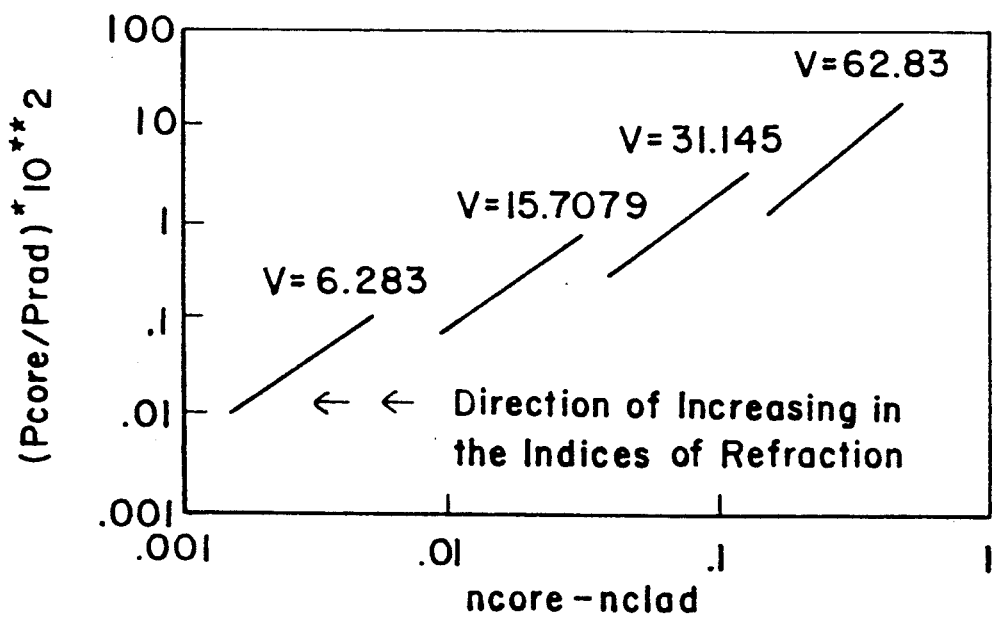
FIG. 3 is a graph of the power efficiency of an optical fluorosensor versus the difference ep between the index of refraction of the fiber core and the index of refraction of the cladding.

FIG. 3 illustrates how the power efficiency of a thin film distribution of sources behaves with the difference $n_{core} - n_{clad}$ at a constant V, a=6.0 μm, b=30.0 μm and λ=0.6 μm. Similar results are obtained for the power efficiency of a bulk distribution of sources. This data was obtained for four different V-numbers and was plotted on a log-log scale. Notice that these curves can easily be fitted into a linear equation. Apparently the higher the V-number the more the graph deviates from a linear equation in a log-log scale. FIG. 3 also shows that the greater the difference between the indices of refraction, the higher the power efficiency. The apparent high value of the power efficiency at high V-number is due not to the increase in this V value, but to bigger differences between the indices of refraction. The upper portion of each curve of FIG. 3 represents the highest power efficiency that can be reached at these particular values, i.e., the index of refraction of the cladding is equal to one, which is the lowest possible index of refraction and the highest possible difference between the indices at V constant. As both indices of refraction increase, the difference between them decreases and the power efficiency decreases. The indices of refraction used in this figure are within the interval $3.5 > n_{core} > n_{clad} > 1.0$. Thus, the lower extremes of each curve corresponds to $n_{core}$=3.5. Notice that the V-numbers used have a very big difference between each other. V-numbers which are closer to each other may possibly generate graphs that obey the increase of the power efficiency at the cut-off value.

From the foregoing, for a given wavelength λ and V-number, an increasing difference in $n_{core}$ and $n_{clad}$ results in a higher power efficiency. Apparently a similar result was obtained for the $TE_{0,\mu}$ modes in Watanabe, A., Hill, K. O. and Mintz, D., "Calculation of Evanescent-Wave Gain in the $TE_{0m}$ and $TM_{0m}$ Modes of an Optical Fibre", Report No. 1247, FIG. 5, Communications Research Centre, Department of Communications, Ottawa, Canada, July, 1973. This result can be explained for the $TM_{0,\mu}$ modes in terms of the amplitude of its electric field. The electric field of $TM_{0,\mu}$ modes in the cladding region is directly proportional to the square of the ratio $n_{core}/n_{clad}$. Since the coefficients are directly proportional to the amplitude of the electric field, the power injected in the core is also directly proportional to this amplitude.

There is a reinforcement in the power efficiency among the $TE_{0,\mu}$, $TM_{0,\mu}$ and $HE_{2,\mu}$ modes of the weakly guiding fiber ($n_{core} \approx n_{clad}$) and a reinforcement between $HE_{1,\mu}$ and $HE_{2,\mu}$ modes of strongly guiding fiber ($n_{core} > > n_{clad}$). Reinforcement occurs because the corresponding modes have the same cut-off frequency in both limits. Since they have the same cut-off frequency, the power efficiency is reinforced near the cut-off.

In general, the longer the wavelength the higher the power efficiency. Apparently, this result reflects the characteristics of the behavior of a wave. In other words the bigger the wavelength with respect to the dimensions of the fiber, the more tunneling from the cladding one should expect. This last result also implies that the lower the V-number the higher the power efficiency, a conclusions which seems to be contrary to the general belief that a higher V-number would yield a higher power efficiency. Apparently there is no error involved in prior published data, but it seems that the interpretation given to the graph of the weakly guiding fiber, i.e., that the power efficiency increases with the V-number, is not correct. Rather, for both the weakly guiding and the general case, the difference between $n_{core}$ and $n_{clad}$, and not the number of modes, is critical. The variation of the indices of refraction with the wavelength was not considered.

Figure 4:
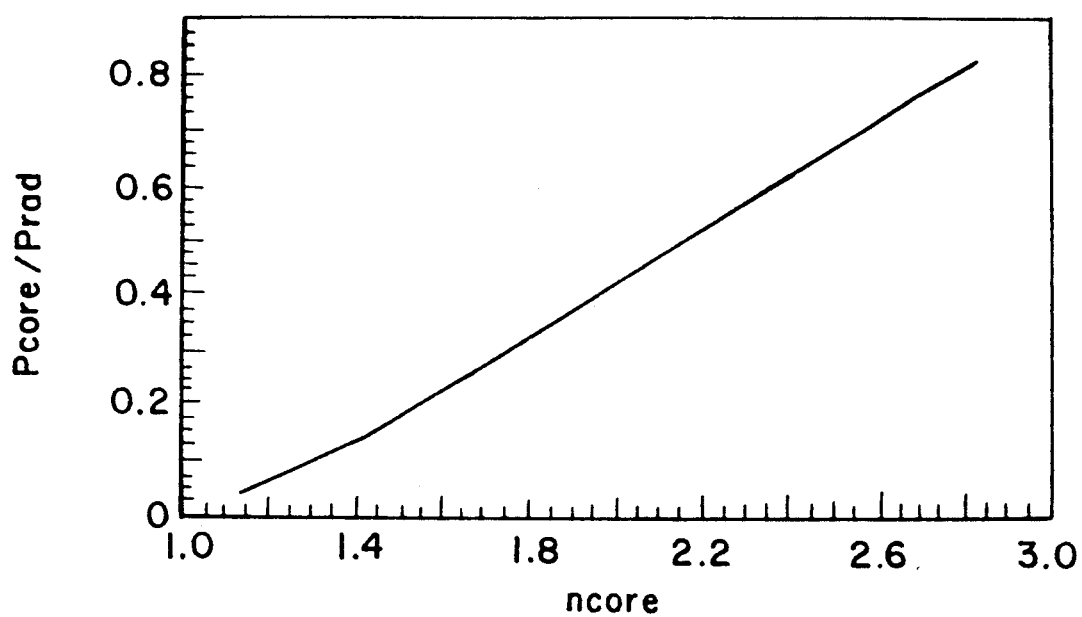
FIG. 4 is a graph of the power efficiency of a thin film sensor as a function of index of refraction of the fiber core.

In the case where the bare fiber core 12 is coated with a very thin film of fluorescent or chemiluminescent material, the fiber can be modeled as a cylindrical rod whose guide cladding is the surrounding air itself, i.e., $n_{clad} = 1.0$. In other words, the coating is assumed to be thin enough so the effect of its index of refraction can be ignored. The surrounding atmosphere, e.g., air, serves as an effective cladding to guide the light into and throughout the core, FIG. 4 graphs the behavior of the power efficiency of this then film optical fiber for a variable $n_{core}$, wherein the V-number is varied from 29.73 to 202.79 and the following variable are held fixed: $a = 5.0 \mu m$, $\lambda = 0.6$ $\mu m$ and $n_{clad} = 1.0$. As expected from the previous discussion, the power efficiency increases with $n_{core}$ since (1) the higher the difference $n_{core} - n_{clad}$, the higher the power efficiency, and (2) $n_{clad}$ is that of air, which has the lowest possible refractive index. The index of refraction of core 12 should be at least approximately 1.01 to achieve an adequate difference in the refraction indices of 0.01. The increase in the power efficiency is almost linear but cannot keep on growing indefinitely. Previous work has found power efficiency as high as 60%, and FIG. 4 shows that it could go even higher, up to approximately 85%. If larger core indices of refraction are used, higher efficiencies should be expected. However, the results discussed refer only to the forward propagating modes of the fiber. Consequently, if both forward and backward propagating modes are taken into account, the final result would exceed the 100% limit of the power efficiency. The correct expression for the total power should include the sum of both forward and backward propagating bound modes yielding the following result for the power efficiency, namely $$P_{eff} = \frac{P_{core}}{P_{rad} + 2P_{core}} \quad (2)$$

compared to $$P_{eff} = \frac{P_{core}}{P_{rad}}. \quad (3)$$

Consequently, equation (2) solves the problem of $P_{eff}$ greater than 100% and equation (3) is still a good approximation whenever $P_{rad} > > > P_{eff}$ or $P_{eff}$ is small enough, namely lesser than 0.1.

The fluorosensor 10 can be attached to or embedded in a desired structure to determine the presence of an analyte. For example, the fluorosensor could be embedded in a graphite-epoxy composite structure such as the proposed Space Station Freedom to sense the presence of potentially damaging atomic oxygen as part of a smart structure. Photons are injected into the core fiber 12 as discussed above and the detected signal in indicative of the concentration of atomic oxygen. Appropriate corrective measures are then initiated to avoid further degradation of the structure.

Many modifications, improvements and substitutions will be apparent to the skilled artisan without departing from the spirit and scope of the present invention as described in the foregoing and defined in the following claims.

What is claimed is:

1. An optical fiber comprising:
   a fiber core;
   an active cladding surrounding a portion of said fiber core, said active cladding capable of producing waves of light which are injected into said fiber core upon excitation; and
   a guide cladding surrounding another portion of said fiber core, whereby said guide cladding guides the produced waves of light throughout said fiber core;
   wherein $n_{core} - n_{clad}$ is greater than 0.01, wherein $n_{core}$ is the index of refraction of said fiber core and $n_{clad}$ is the index of refraction of said guide and said active cladding.

2. The optical fiber according to claim 1, wherein said active cladding comprises a matrix containing substances capable of producing the evanescent waves of light.

3. The optical fiber according to claim 2 wherein the substances are fluorescent substances which are excited to produce light via an outside source of light.

4. The optical fiber according to claim 2, wherein the substances are chemiluminescent substances.

5. An optical fiber fluorosensor for use in sensing the concentration of an analyte, comprising:
   a fiber core;
   an active cladding surrounding a portion of said fiber core, said active cladding comprising a matrix which is permeable by the analyte and substances located in the matrix which are capable upon excitation of producing waves of light which are injected into said fiber core; and
   a guide cladding surrounding another portion of said fiber core, whereby said guide cladding guides the produced waves of light throughout said fiber core to a sensor which senses the intensity of the light waves as an indication of the concentration of the analyte outside of said cladding;

wherein $n_{core} - n_{clad}$ is greater than 0.01, wherein $n_{core}$ is the index of refraction of said fiber core and $n_{clad}$ is the index of refraction of said guide and said active cladding.

6. The fluorosensor according to claim 5, wherein the substances are fluorescent substances which are excited to produce light via an outside source of light.

7. The fluorosensor according to claim 5, wherein the substances are chemiluminescent substances which emit light when excited by a chemical reaction with the analyte.

8. A thin film optical fiber surrounded by a gaseous atmosphere comprising:

a fiber core; and an active cladding surrounding said fiber core which upon excitation is capable of producing waves of light which are injected into said fiber core;

wherein said active cladding is thin enough such that its index of refraction is effectively that of the gaseous atmosphere, whereby the gaseous atmosphere guides the produced waves of light throughout said fiber core; and wherein the differences between the respective indices of refraction of said fiber core and the gaseous atmosphere is greater than 0.01.

9. The thin film optical fiber according to claim 8, wherein said active cladding comprises a matrix containing substances capable of producing the evanescent waves of light.

10. The thin film optical fiber according to claim 8 wherein the substances are fluorescent substances which are excited to produce light via an outside source of light.

11. The thin film optical fiber according to claim 8, wherein the substances are chemiluminescent substances.

12. The thin film optical fiber according to claim 8, wherein air surrounds the optical fiber and the effective index of refraction of the active cladding is 1.0.

13. A thin film optical fiber fluorosensor for use in sensing the concentration of an analyte in a gaseous atmosphere surrounding the optical fiber, the optical fiber comprising:

a fiber core; and an active cladding surrounding said fiber core, said active cladding comprising a matrix which is permeable by the analyte and substances located in the matrix which are capable upon excitation of producing waves of light which are injected into said fiber core;

wherein said active cladding is thin enough such that its index of refraction is effectively that of the gaseous atmosphere, whereby said gaseous atmosphere effectively guides the produced waves of light throughout said fiber core to a sensor which senses the intensity of the light waves as an indication of the concentration of the analyte in the gaseous atmosphere; and wherein the difference between the respective indices of refraction of said fiber and the gaseous atmosphere is greater than 0.01.

14. The thin film fluorosensor according to claim 13, wherein the substances are fluorescent substances which are excited to produce light via an outside source of light.

15. The thin film fluorosensor according to claim 13, wherein the substances are chemiluminescent substances which emit light when excited by a chemical reaction with the analyte.

16. The thin film fluorosensor according to claim 13, wherein air surrounds the optical fiber and the effective index of refraction of the cladding is 1.0.

17. A method of improving the power efficiency of an optical fiber comprising:

providing a fiber core;

providing an active claddig surrounding a portion of said fiber core, said active cladding capable of producing waves of light which are injected into said fiber core upon excitation; and providing a guide cladding surrounding another portion of said fiber core, whereby said guide cladding guides the produced waves of light throughout said fiber core; wherein the guide cladding, active cladding and fiber core are selected such that $n_{core} - n_{clad}$ is greater than 0.01, wherein $n_{core}$ is the index of refraction of said fiber core and $n_{clad}$ is the index of refraction of said guide and said active cladding.

18. A method of improving the power efficiency of an optical fiber fluorosensor for use in sensing the concentration of an analyte, comprising:

providing a fiber core;

providing an active cladding surrounding a portion of said fiber core, said active cladding comprising a matrix which is permeable by the analyte and substances located in the matrix which are capable upon excitation of producing waves of light which are injected into said fiber core; and providing a guide cladding surrounding another portion of said fiber core, whereby said guide cladding guides the produced waves of light throughout said fiber core to a sensor which senses the intensity of the light waves as an indication of the concentration of the analyte outside of said cladding;

wherein the guide cladding, active cladding and fiber core are selected such that $n_{core} - n_{clad}$ is greater than 0.01, wherein $n_{core}$ is the index of refraction of said fiber core and $n_{clad}$ is the index of refraction of said guide and said active cladding.

* * * * *